United States Patent [19]

DelliColli

[11] Patent Number: 4,752,319
[45] Date of Patent: Jun. 21, 1988

[54] SEED TREATMENT METHOD WITH AQUEOUS SUSPENSION OF ALKALI LIGNIN

[75] Inventor: Humbert T. DelliColli, Hanahan, S.C.

[73] Assignee: Westvaco Corporation, New York, N.Y.

[21] Appl. No.: 757,170

[22] Filed: Jul. 22, 1985

Related U.S. Application Data

[62] Division of Ser. No. 523,405, Aug. 15, 1983, Pat. No. 4,624,694.

[51] Int. Cl.$^4$ ............................................. A01N 65/00
[52] U.S. Cl. ............................................. 71/77; 71/79; 71/DIG. 1; 47/57.6
[58] Field of Search ..................... 47/57.6; 71/DIG. 1, 71/77

[56] References Cited

U.S. PATENT DOCUMENTS

| | | | |
|---|---|---|---|
| 2,651,883 | 9/1953 | Hedrick et al. | 47/1 |
| 2,678,878 | 5/1954 | Stewart | 71/77 |
| 3,598,565 | 8/1971 | Graves | 71/77 |
| 3,617,247 | 11/1971 | Chiles, Jr. | 71/77 |
| 3,674,458 | 7/1972 | Schattner | 71/77 |
| 3,726,850 | 4/1973 | Detroit | 260/124 A |
| 3,813,236 | 5/1974 | Allan | 71/94 |
| 3,929,453 | 12/1975 | Dimitri et al. | 71/101 |
| 3,992,532 | 11/1976 | Dimitri | 424/213 |
| 4,116,666 | 9/1978 | Willard, Sr. | 71/77 |
| 4,184,866 | 1/1980 | DelliColli et al. | 71/65 |
| 4,244,728 | 1/1981 | DelliColli et al. | 71/65 |
| 4,244,729 | 1/1981 | DelliColli et al. | 71/65 |
| 4,245,432 | 1/1981 | Dannelly | 47/57.6 |
| 4,310,348 | 1/1982 | Budai et al. | 71/77 |
| 4,381,194 | 4/1983 | DelliColli et al. | 71/DIG. 1 |
| 4,404,015 | 9/1983 | Menon et al. | 71/77 |

FOREIGN PATENT DOCUMENTS 0327914  3/1972  U.S.S.R. ................................. 71/77

OTHER PUBLICATIONS

Sharunova, "Presowing Treatment of Lilac Seeds with Growth Stimulants," Chem. Abs., 73:65231c (1971).

*Primary Examiner*—Glennon H. Hollrah
*Assistant Examiner*—Patricia L. Morris
*Attorney, Agent, or Firm*—Terry B. McDaniel; Richard L. Schmalz

[57] ABSTRACT

A method of crop seed treatment is disclosed which provides an increase in the yield of seedlings emerging from the treated seeds in soil and stimulates growth of the seedlings. The method comprises coating the seeds prior to planting with an aqueous suspension of water-insoluble alkali lignin containing minor amounts of at least one surfactant wherein the lignin has a mean particle size of from 0.5 to 5 microns in diameter.

2 Claims, No Drawings

SEED TREATMENT METHOD WITH AQUEOUS SUSPENSION OF ALKALI LIGNIN

This is a division of application Ser. No. 523,405 filed Aug. 15, 1983 now U.S. Pat. No. 4,624,694.

BACKGROUND OF THE INVENTION

1. Field of the Invention

The invention relates to a method of increasing the yield of seedlings emerging from seeds in soil and stimulating growth of the seedlings by coating the seeds prior to planting with an aqueous suspension of a water-insoluble alkali lignin. The lignin suspension contains minor amounts of at least one surfactant and the lignin has been ground to a mean particle size of from 0.5 to 5 microns in diameter.

2. Description of the Prior Art

The pelleting, or coating, of seeds was originally designed to produce units of uniform size and shape capable of being drilled singly at any desired distance, thereby eliminating the need for thinning the seedlings. But such pellets have the added advantage of providing seeds with an enlarged bulk, so they can carry in this package whatever chemicals it is desired to apply, both in reasonably large amounts and not in the most intimate contact with the seed itself, thus avoiding possible phytotoxic effects.

U.S. Pat. No. 2,651,883 reports that water-soluble synthetic polyelectrolytes may be used as the resinous binders for coating compositions for seeds. The water-soluble synthetic polyelectrolytes have a substantially continuous carbon chain derived by the polymerization of an aliphatic unsaturated carbon to carbon linkage and have weight average molecular weights in excess of 10,000. The patent also reports an increase in germination of the coated seeds and enhanced growth characteristics of the plant.

U.S. Pat. No. 3,598,565 teaches a coating composition for treating seeds comprising an aqueous emulsion of a substantially water-soluble neutralized copolymer of an $\alpha,\beta$-unsaturated monocarboxylic acid and a lower alkyl acrylate and a crosslinked copolymer of vinyl acetate and a lower alkyl acrylate, which compositions enhance the germination of the coated seeds.

U.S. Pat. No. 3,617,247 teaches seeds coated with carbamylalkenyl phosphorus-containing ester insecticides which act not only in their known insecticidal capacity but enhance the growth of the seedlings and produce an increased ultimate yield of the crop planted.

U.S. Pat. No. 3,674,458 provides a method of regulating the growth of plants involving the treating of seeds with an aqueous solution comprising sodium phenolate, sodium tetraborate, phenol and a humectant, before planting.

There is no known teaching in the prior art of lignin as a seed coating material, although the use of lignin in pesticide formulations as a surfactant or as part of the pesticide delivery system (i.e., as a carrier) is known.

In U.S. Pat. No. 3,726,850, Detroit teaches water-soluble, ozone-oxidized alkali lignin to be pesticide dispersants. U.S. Pat. No. 3,992,532 discloses a method for providing a flowable pesticide formulation with such rheological properties so as to reduce or eliminate sedimentation and liquid phase separation of insoluble pesticides by mixing alkali lignin and liquid toxicant with a hydrocarbon oil and subjecting the mixture to high shear.

U.S. Pat. No. 3,813,236 discloses the chemical covalent bonding of a pesticide to a lignin polymeric substrate. The pesticide is controllably released by destruction of the covalent chemical bonds. U.S. Pat. No. 3,929,453, reissued as Re. No. 29,238, teaches a slow release lignin composite obtained by the coprecipitation-inclusion from an aqueous alkaline lignin solution by adding acid or salts, the drying of a precipitated lignin slurry/pesticide dispersion, or the elimination of a common solvent from a lignin-pesticide mixture.

In other sustained release compositions, U.S. Pat. Nos. 4,184,866, 4,244,728 and 4,244,729, all of which have as a co-inventor the inventor in this application, teach an improved pesticide carrier made by cross-linking an alkali lignin with epichlorohydrin or formaldehyde.

Finally, U.S. Pat. No. 4,381,194, which also has as a co-inventor the inventor in this application, discloses a method for protecting crops from the phytotoxic effect of herbicides and fungicides. The patent teaches combining the herbicide or fungicide with an aqueous suspension concentrate of a water-insoluble alkali lignin containing minor amounts of at least one surfactant wherein the lignin has a mean particle size of from 0.5 to 5 microns in diameter.

Collectively, the prior art relating to agricultural uses of lignin teaches the application of lignin to crops in combination with a pesticide or as a part of a pesticide delivery system. Therefore, the beneficial effects of applying only water-insoluble alkali lignin directly onto seeds resulting in growth stimulation and increased yield of the seedlings was surprising and unexpected.

It is the object of this invention to provide a method of seed treatment wherein seeds are coated prior to planting by contacting the seeds with an aqueous suspension of a water-insoluble alkali lignin, preferably by mixing the seeds in the suspension followed by drying. The alkali lignin suspension contains minor amounts of at least one surfactant and the lignin thereof has a mean particle diameter of from 0.5 to 5 microns.

SUMMARY OF THE INVENTION

This invention provides a method of crop seed treatment which increases the yield of seedlings emerging from the treated seeds in soil and stimulates growth of the seedlings. The method comprises coating the seeds prior to planting with an aqueous suspension of a water-insoluble alkali lignin containing minor amounts of at least one surfactant wherein the lignin has a mean particle size of from 0.5 to 5 microns in diameter.

DESCRIPTION OF THE PREFERRED EMBODIMENTS

The water-insoluble, non-sulfonated alkali lignin of the invention is the lignin disclosed in U.S. Pat. No. 4,381,194, which teaching is incorporated by reference herein. It is the lignin derived from the kraft papermaking process refined to its acid form, Indulin ® A, as opposed to its water-soluble salts, also produced commercially as Indulin ® B and Indulin ® C by Westvaco Corporation.

The pseudoplastic suspension concentrate of water-insoluble alkali lignin is prepared in water with minor amounts of selected conventional surfactants including humectants, wetting agents, dispersing agents and/or antifreeze agents. To achieve the desired dispersed suspension, the granular lignin is ground or milled to a powder with a mean particle size of a particle diameter of from 0.5 to 5.0 microns, as determined by dark field microscope.

The particle size range of from 0.5 to 5 microns in particle diameter has been determined to be critical for maintaining the aqueous suspension shelf life. An average particle size of less than 0.5 microns in diameter results in gelling of the suspension. An average lignin particle size greater than 5 microns in diameter may result in the lignin material precipitating out of the suspension.

The utilization of supplemental agents having wetting, dispersing and/or suspending properties is widespread in the preparation of agricultural formulations to render water-insoluble substances dispersible in water. Ideally, the formulations are fast wetting when dispersed in water and form suspensions with relatively high solids content which are low foaming and do not exhibit tendencies toward sedimentation with age. Satisfactory humectants employed in the water-insoluble, non-sulfonated alkali lignin suspension concentrate are glycerol, saccharinic acids and ethoxylated glycerides, with glycerol being preferred. Various commercially available soaps, detergents and surface active agents may be employed as a wetting agent. One or more of the following are preferred: di 2-ethylhexyl sodium sulfosuccinate, sodium 2-ethyl sulfate and mixtures thereof, sold under the trade names ROE 55 and Valchem 329-104.

Suitable dispersing agents are water-soluble lignin sulfonates and alkyl naphthalene sulfonates. Water-soluble sulfonated lignins can be lignosulfonates from the sulfite process of wood pulping or an alkali salt of a sulfate lignin which has been sulfonated, such as Polyfon® H, sold by Westvaco Corporation. Likewise, the alkyl naphthalene sulfonates are well known in the art and are used in the form of their alkali metal or ammonium salt.

To lower the freezing point of the aqueous suspension, antifreeze agents such as propylene glycol, methanol and ethylene glycol are employed, with propylene glycol being preferred.

As can be appreciated by those in the art, in preparing the flowable formulations of the present invention, supplemental agents functioning as water-conditioning agents, thickening agents, and the like suitably may be added.

In preparing the flowable formulations of the invention, the ingredients employed suitably may be combined in various sequences in conventional mixing means. However, it is usually necessary to add at least a portion of one of the liquid ingredients to the granular water-insoluble alkali lignin prior to introduction into the ball mill, as it is difficult to achieve the desired lignin particle size in a dry grind.

The invention having been broadly described, the examples to follow are given to show specific embodiments thereof.

The water-insoluble alkali lignin formulation of this invention is prepared by first adding water to the lignin to form an aqueous slurry and drying the slurry to from about 2% to about 5% moisture. Add from about 1% to about 10% by volume of one or more of the conventional surfactants listed above to the essentially dry slurry and grind the slurry to an average particle size of from 0.5 to 5 microns in diameter by attrition grinding. The preferred surfactants are a mixture of wetting agents (di 2-ethylhexyl sodium sulfosuccinate and sodium 2-ethyl sulfate) and a dispersing agent (water-soluble lignin sulfonate).

EXAMPLE 1

Wheat seed of the Authur 51 variety was coated with a water-insoluble alkali lignin slurry made according to the above procedure at the rate of one quart of lignin slurry (34% "A" lignin solids) per 60 lbs of seed. This was accomplished by tumbling the seed in the presence of the lignin slurry in a cement mixer for a period of 5 minutes. After being coated, the seed was spread on a screen and dried for three hours.

After drying, the seed was planted using a John Deere planter.

A control treatment consisting of uncoated seed of the same variety was planted in the same field. Test and control plots were laid out in alternating strips.

Germination occurred within both test and control plots in six days. Shortly after germination, seedlings emerging from lignin coated seed began to take on a chlorotic stunted appearance while seedlings emerging from uncoated seed appeared normally green and about the same size as plants of this same variety from other fields immediately adjacent to the test site.

This visual difference between test and control plots remained throughout the prevernalization and vernalization periods. Approximately twelve weeks after planting, when the wheat began to grow out of its dormant period, the wheat from coated seed grew out of its chlorotic and stunted state. By sixteen weeks after planting, test plants had outgrown the controls. At this time ground coverage by control plants was estimated to be 60–70% while coverage by test plants was estimated to be in excess of 95%.

When the plants produced seed heads, test plants averaged 11 seedheads per plant and controls averaged 7.5.

At maturity, which occurred 7–10 days earlier on the test plots than on the control, control plants were more spindly and taller than the fuller developed test plants by about 3 inches. Harvest took the form of sub-sampling of a series of 0.01 acre sub-plots within the field from randomly selected areas. The harvest data are reported in Table I below:

TABLE I

| HARVEST YIELD DATA (lbs/plot) | |
|---|---|
| Control (uncoated seed) | Test (coated seed) |
| 22.0 | 27.5 |
| 28.5 | 32.0 |
| 26.0 | 34.0 |
| 25.0 | 33.0 |
| 24.0 | |
| 27.0 | |
| 24.0 | |
| Calculated Mean* | |
| 25.2 lbs/plot<br>42.3 Bu/A<br>(test wt. 60 lbs/Bu)** | 31.6 lbs/plot<br>53.5 Bu/A<br>(test wt. 59 lbs/Bu)** |

| | |
|---|---|
| *Analysis of Variance | |
| Mean square (within treatments) = | 5.846 |
| Mean square (between treatments) = | 104.6 |
| F ratio = | 17.89 |
| df (degrees of freedom) = | 1,9 |
| Level of significance $\alpha$= | 0.002 |

**Conversion factor to correct for moisture content

The observed effects of inhibited early development followed by accelerated growth with yield increases are not fully understood and may not occur with all seeds, as noted in Example 2, below.

EXAMPLE 2

DeKalb-Sudax-Sorghum-Sudan grass seed variety was coated at a ratio of 2 quarts of water-insoluble alkali lignin aqueous slurry to thirty pounds of seed. The seed and slurry were hand mixed and air dried for three hours. Four days after coating the seeds were planted simultaneously with uncoated seeds as a control. Emergence from treated and control seeds occurred within seven days. But the accelerated growth of treated seed relative to the untreated seed (control) was observed immediately after emergence. In this experiment, no period of chlorosis, or inhibited growth, was noted.

As will be evident to those skilled in the art, various modifications on this invention can be made or followed, in the light of the foregoing disclosure and discussion, without departing from the spirit or scope of the disclosure or from the scope of the following claims.

What is claimed is:

1. A coated seed product comprising a seed having adhered thereto, in an amount effective to accelerate the growth of the seed, a composition formed by adding to a water-insoluble alkali lignin, in the form of a lignin aqueous slurry of from about 2% to about 5% moisture, from about 1% to about 10% by volume, of a member of the group consisting of a humectant, a wetting agent, a dispersing agent, an antifreeze agent, and mixtures thereof wherein the lignin has a mean particle size of from 0.5 to 5 microns in diameter.

2. The coated seed product of claim 1 wherein the member is a mixture of di 2-ethylhexyl sodium sulfosuccinate, sodium 2-ethyl sulfate, and water-soluble lignin sulfonate.

* * * * *